(12) United States Patent
Austin et al.

(10) Patent No.: US 7,080,555 B2
(45) Date of Patent: Jul. 25, 2006

(54) DISTRIBUTED MODE SYSTEM FOR REAL TIME ACOUSTIC EMISSION MONITORING

(75) Inventors: Russell K. Austin, Austin, TX (US); Chris Coughlin, Austin, TX (US)

(73) Assignee: Texas Research International, Inc., Austin, TX (US)

(*) Notice: Subject to any disclaimer, the term of this patent is extended or adjusted under 35 U.S.C. 154(b) by 48 days.

(21) Appl. No.: 10/862,096

(22) Filed: Jun. 4, 2004

(65) Prior Publication Data
US 2006/0032313 A1    Feb. 16, 2006

(51) Int. Cl.
*G01N 29/14* (2006.01)

(52) U.S. Cl. ............................ 73/587; 73/594; 702/36; 702/35

(58) Field of Classification Search ................. 73/583, 73/587, 594; 702/35, 36
See application file for complete search history.

(56) References Cited

U.S. PATENT DOCUMENTS

| 3,985,024 | A |  | 10/1976 | Horak |
|---|---|---|---|---|
| 4,459,851 | A | * | 7/1984 | Crostack ...................... 73/587 |
| 4,910,718 | A |  | 3/1990 | Horn |
| 4,956,999 | A | * | 9/1990 | Bohannan et al. ............ 73/587 |
| 5,129,063 | A | * | 7/1992 | Sainola et al. ................. 710/1 |
| 5,195,046 | A | * | 3/1993 | Gerardi et al. ................ 702/35 |
| 5,293,555 | A | * | 3/1994 | Anthony ....................... 702/36 |
| 5,383,133 | A | * | 1/1995 | Staple ......................... 700/280 |
| 5,544,308 | A | * | 8/1996 | Giordano et al. ............ 714/26 |
| 5,675,506 | A | * | 10/1997 | Savic ........................... 702/51 |
| 6,014,896 | A |  | 1/2000 | Schoess |
| 6,076,405 | A |  | 6/2000 | Schoess |
| 6,192,759 | B1 | * | 2/2001 | Schoess ....................... 73/583 |
| 6,399,939 | B1 | * | 6/2002 | Sundaresan et al. ..... 250/231.1 |
| 6,443,012 | B1 |  | 9/2002 | Beardmore |
| 6,449,565 | B1 |  | 9/2002 | Budrow |
| 6,531,965 | B1 | * | 3/2003 | Kaiser et al. .......... 340/870.01 |
| 2003/0003872 | A1 | * | 1/2003 | Brinkley et al. .............. 455/66 |

* cited by examiner

*Primary Examiner*—Hezron Williams
*Assistant Examiner*—Rose M. Miller (57) ABSTRACT

A distributed real time health monitoring system is described for monitoring of acoustic emission signals from different regions of a structure such as aircraft or spacecraft structures. The health monitoring system has its analysis and prognosis intelligence distributed out to the local regions being monitored and therefore does not require extensive cabling systems to carry the high bandwidth information characteristic of acoustic emission.

25 Claims, 6 Drawing Sheets

DISTRIBUTED MODE SYSTEM FOR REAL TIME ACOUSTIC EMISSION MONITORING

STATEMENT REGARDING FEDERALLY SPONSORED R&D

This invention was made with government support under N00421-99-C-156 awarded by the Naval Air Systems Command and W31 P4Q-04-C-R041 awarded by the U.S. Army. The federal government has certain rights to the invention.

TECHNICAL FIELD

The invention relates generally to the field of acoustic emission monitoring of structures.

BACKGROUND

Acoustic emission (AE) is a proven non-destructive evaluation (NDE) protocol for monitoring the integrity of structures. A number of NDE methods are available to detect fatigue cracks in structures and each method has one or more significant technical limitations. These NDE methods include visual, tap, ultrasonic, eddy current, and x-ray radiography. Visual inspection is appropriate for checking for surface cracks but inadequate for detecting sub-surface cracks. Eddy current technology can detect cracks but requires a trained NDE technician to properly position eddy current probes and to interpret the test results. X-ray radiography is effective but requires specialized equipment and for safety reasons limits human access to the equipment while the testing is underway. None of these methods are conducive to real time monitoring for providing early warning indications of structural cracks.

Acoustic emission methodology uses an acoustic emission transducer to "listen" for the first signs of the formation of a crack in a structure. Acoustic emission energy is a transient elastic stress wave generated by the rapid release of energy from a localized source within a material. There are many sources of AE that can be recorded for NDE purposes: crack formation and growth, magneto-mechanical realignment or growth of magnetic domains, microstructure changes such as dislocation movement, phase changes, fracture of brittle inclusions or surface films, or even chemical activity resulting from corrosion. Non-destructive evaluation applications of AE basically involve "listening" for sound generated by growing damage in a test piece. Although AE's are generated by the material itself and not by an external source, a stimulus is usually needed to trigger the original AE. These stimuli are sometimes applied by magnetic, thermal, chemical, or mechanical means. When these stimuli are artificially implied for purposes of the test they are sometimes called "active" methods. It is also possible to listen for AE events during in-service use of the structure and this approach is sometimes referred to as a "passive" method.

Traditional AE is widely used and standardized in the oil, petrochemical and rail industries. It has also been used to monitor aircraft structures during ground tests, full-scale fatigue tests, and intermittent flight tests. The traditional implementation equipment is heavy however, often greater than 20 pounds, and large enough to be unsuitable for continuous in-flight use. Traditional AE systems also run a cable from each and every AE transducer all the way back to the centralized computer system. These cable systems require a high bandwidth because of the extensive data transmission required. In addition the traditional implementation transfer an analog signal from the transducer to the central computer. Transferring analog signals over long cable runs increases the likelihood that electrical noise will interfere with the signal. Electrical noise, also called electromagnetic interference, or EMI, is unwanted electrical signals that produce undesirable effects and otherwise disrupt the control system circuits. There is also the potential for radio frequency interference (RFI) from the potential power transfer densities involved due to the proximity of equipment and antenna systems on modern aircraft.

In today's economy aircraft structures must remain in operation for much longer periods of time than originally anticipated. Accordingly the aging effects on these structures are becoming more significant and must be accounted for in the decisions made regarding usage, maintenance, and retirement of the structures. Ideally a real-time in-service monitoring system is needed. Acoustic emission monitoring has great potential for providing in-service monitoring of damage accumulation in this application. AE transducers are small and lightweight and can be permanently mounted. AE data is generated by damage regardless of the size of the individual defect. AE signals created by a flaw propagate through the overall component. If an array of AE transducers is laid out properly, the entire structure can be monitored. Today, however, there is no current real time commercial implementation available due to the aforementioned limitations that current systems are much too large, heavy, and require extensive heavy cabling runs to carry the analog signals back to a central computer. There is thus a long felt need for an implementation of acoustic emission technology that can be used routinely in real time in aircraft structures to either provide warning signals in the cockpit or provide warning diagnostics to maintenance crews at the conclusion of each flight.

U.S. Pat. No. 3,985,024 to Horak is an early AE system developed by Grumman Corporation. It discloses methods for placing AE transducers in ways that enable more accurate predictions of AE source locations. U.S. Pat. No. 4,910,718 to Horn is an AE system specifically designed to locate an AE source in a structural member.

U.S. Pat. No. 6,443,012 to Beardmore discloses a phased array sensing system for an aircraft that includes a central computer and a display system in the cockpit. The matrix arrays are composed of a square or rectangular array of multiple PZT material blocks that are actively pulsed to generate acoustic waves through the structure. The analysis of the AE data is not described other than it is based on imaging technology.

U.S. Pat. Nos. 6,076,405 and 6,014,896, both to Schoess, disclose a remote self-powered AE monitor which has a single AE transducer and still has a centralized computer but eliminates the cabling system by use of a antenna module that sends a continuous stream of data from the acoustic emission transducer to that centralized computer and includes a radio frequency telemetry circuit to supply power to a power storage device with the power storage device positioned on the transducer to provide an inertial load.

The systems described in these patents are either not designed for an array of multiple transducers (U.S. Pat. Nos. 6,076,405 and 6,014,896) or they involve long cable runs to a large centralized computer system. None have been found suitable for commercial applications for aircraft, particularly smaller fighter aircraft, which have little free space for new complex systems. One smaller system is commercially known. The microDiSP from Physical Acoustics Corporation is a smaller portable battery operated acoustic emission system. The chassis of this system though is still 16 inches by 9.5 inches by 2.9 inches high, requires a notebook computer to operate, and does not address the sensor cabling issue outlined above.

What is needed then is a new approach that provides full analysis performance for an array of acoustic transducers that can be implemented in real time on an aircraft while taking up little room and requiring no long cable runs back to a central computer.

SUMMARY

These and other needs are addressed by the present invention. The needs are addressed by changing from a traditional AE system that connects a number of AE transducers via extensive cabling to a centralized computer system that then performs data acquisition and analysis of the raw data to identify and classify AE events and then produce a report or visual display of the results. The approach of the instant invention is to instead distribute all of the acquisition and processing of AE data out to individual distributed microelectronic stations that can each handle multiple AE transducers. Each of these microelectronic stations is a small, independent four to eight channel AE system on a small circuit board. Included on that board is specialized AE acquisition and analysis software that identifies AE events and makes diagnostic and prognostic assessments based on previous extensive testing. Rather than send high bandwidth AE transducer data through multiple cables to a centralized computer the instant invention moves the intelligence out to each distributed transducer array and having classified the resulting AE events from that array either stores the results for future monitoring and/or sends only a simple rating of the health of the structure being monitored to a recording mechanism. A key feature of such an implementation is that no human expert be needed to interpret the data, as is traditional approaches.

One aspect of the instant inventions is then a distributed acoustic emission monitoring system for real time monitoring of acoustic emission signals from a structure wherein each distributed acoustic emission monitoring system includes at least one acoustic emission transducer for detecting said acoustic emission signals, and a microcomputer system that includes at least computer memory, data acquisition software to acquire the raw data and find acoustic emission events, and data analysis software to assess the health of the system/structure and suggest course of action.

Another aspect of the instant invention is a method for the continued real time health monitoring of a structure using acoustic emission analysis including at least the steps of fixedly mounting at least one acoustic emission transducer in a region of the structure to be monitored; distributing, in that same region, a distributed health monitoring system containing all necessary hardware and software for complete analysis of the raw acoustic emission signals from the at least one transducer; amplifying the voltage signals received from the at least one acoustic emission transducer to produce an amplified signal; filtering the amplified signal to eliminate unwanted frequencies to produce a filtered signal; acquiring, during a pre-determined time period, the filtered signal to identify and record acoustic emission events; diagnosing, from the recorded acoustic emission events for the pre-determined time period, the overall health assessment of the region of the structure.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Figure 1:
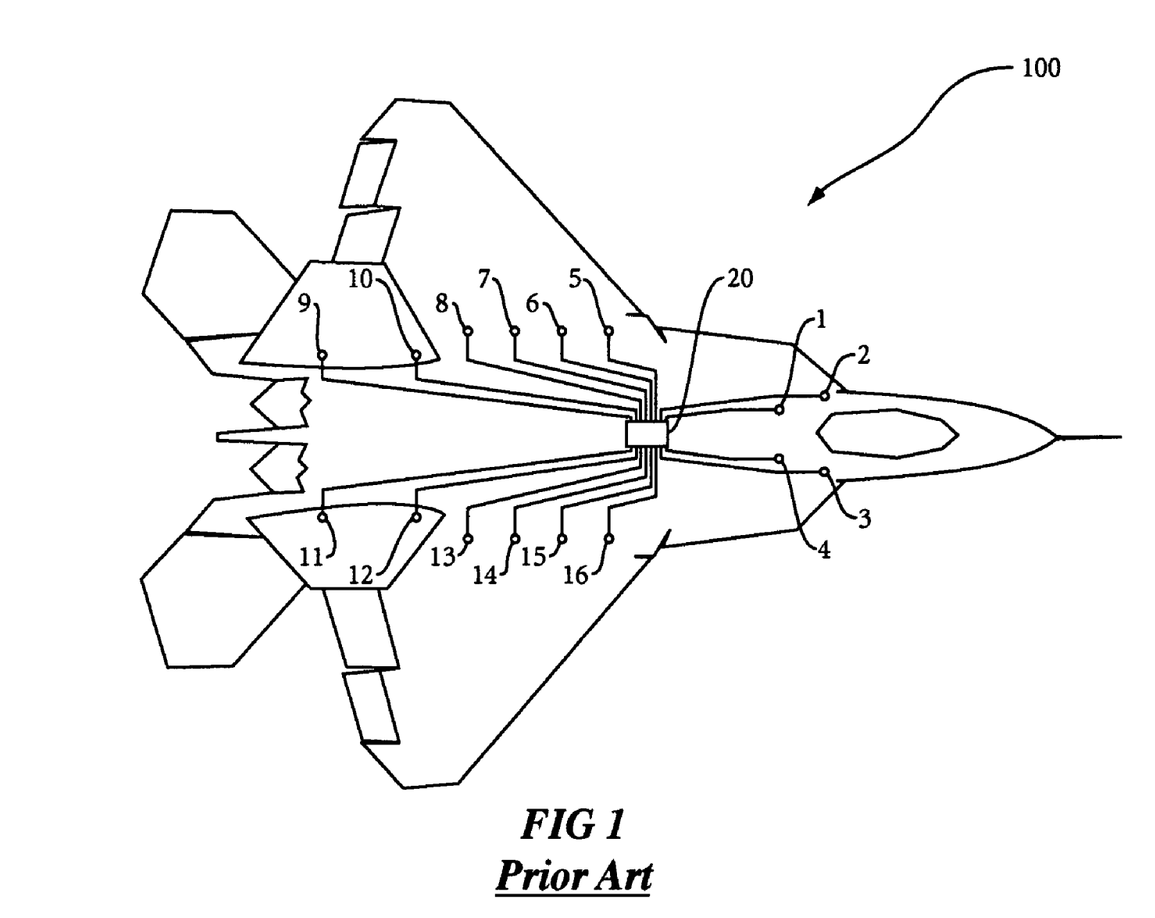
FIG. 1 is representation of the use of prior art centralized AE analysis systems for an aircraft.

FIG. 1 is a typical representation of the prior art. It should be emphasized again that this prior art solution is not being commercially used for real time monitoring because of its impracticality. Represented generally by the numeral 100 is a rendition of the F/A-22. In this example it is assumed for simplicity that a total of 16 acoustic emission transducers are needed to monitor 4 major areas of the aircraft. Four of these 1,2,3,4 are monitoring regions near the cockpit. Four more 5,6,7,8 are monitoring the left wing near its attachment to the fuselage. Another four are monitoring the right wing near its attachment to the fuselage. And the final four are monitoring the wing struts at the rear of the plane. In such an arrangement 16 long cable runs would have to be laid out all over the plane to carry the high bandwidth information to a central computer 20. As mentioned in the background discussion, such systems are not in practical commercial use due to the aforementioned limitations. An alternative to the use of the cabling systems would be to feed the information from the sixteen transducers to the airplanes avionics bus and transmit the information over the bus to a central computer. This has also not been deemed to be a feasible solution, as it would add a large amount of electrical signals to the avionics bus with possible conflicts with the other information being carried there. A typical acoustic emission transducer sends about 10 million voltage signals per second to a central computer.

Figure 2:
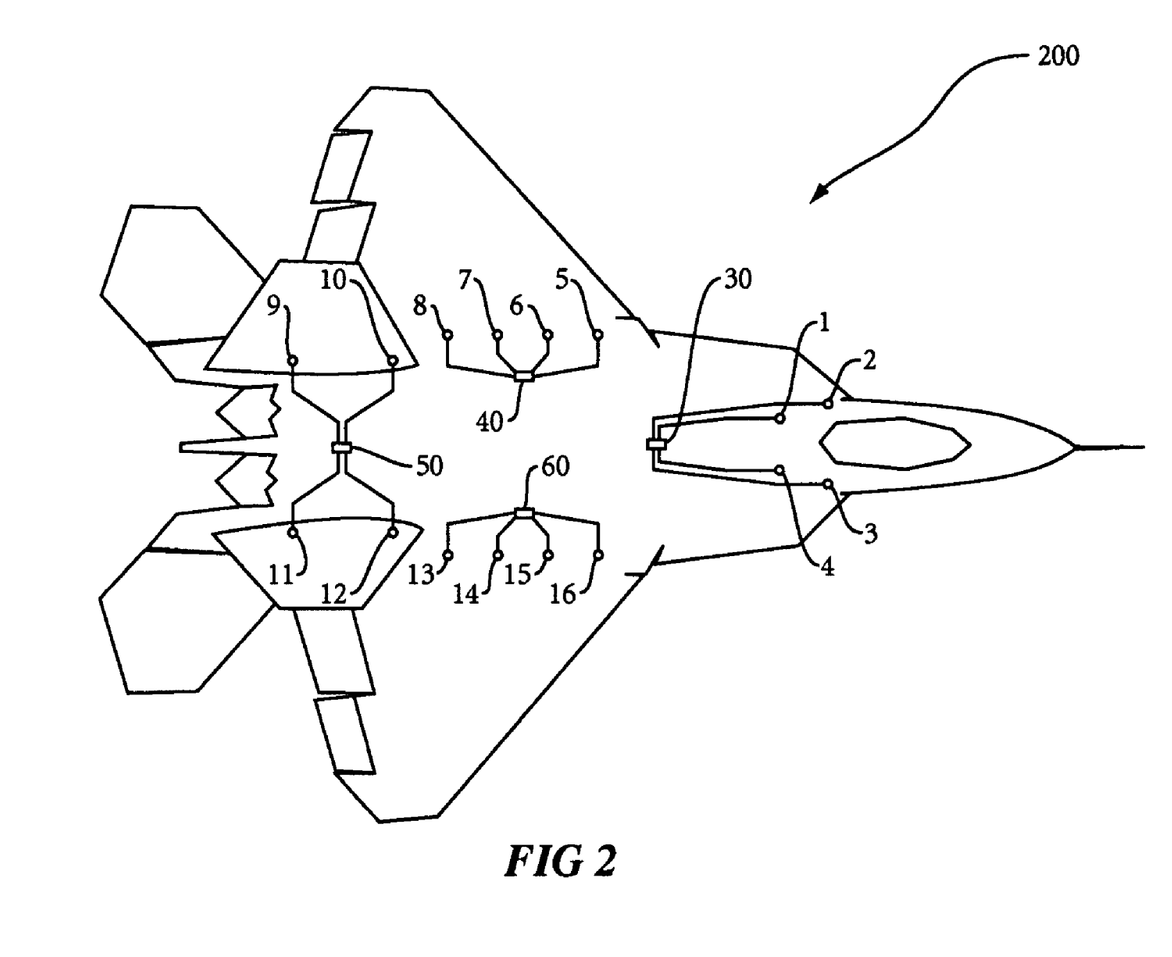
FIG. 2 is a representation of the use of a distributed analysis system such as the instant invention.

FIG. 2 is the solution of the instant invention. Represented generally by the numeral 200 is another rendition of the F/A-22. Four very small LAHMP's (Large Area Health Processing Monitors) each handling four channels are placed on the plane. Each is attached to four transducers 30,40,50,60 by short run cabling. No central computer and no long run cabling is needed. This significant improvement is achieved by innovations in both hardware and software. Each LAHMP contains a small microprocessor with all of the intelligence needed to collect, analyze, and diagnose acoustic emission events. The very large amount of continuous data fed in from acoustic emission transducers, which would normally be stored and processed by a centralized computer is transformed within the LAHMP into a very concise reporting format that can be easily stored in the LAHMP memory over multiple flights for later monitoring on the ground or can be wirelessly transmitted for display in the cockpit if desired. The much larger raw transducer data set is continuously discarded after it has been processed and diagnosed.

A number of acoustic emission transducers are in commercial use today. The practice of the instant invention assumes the use of any of them. Two of the most common are the ceramic piezoelectric transducer and the piezoelectric polyvinylidene fluoride (PVDF) based transducer.

Figure 3:
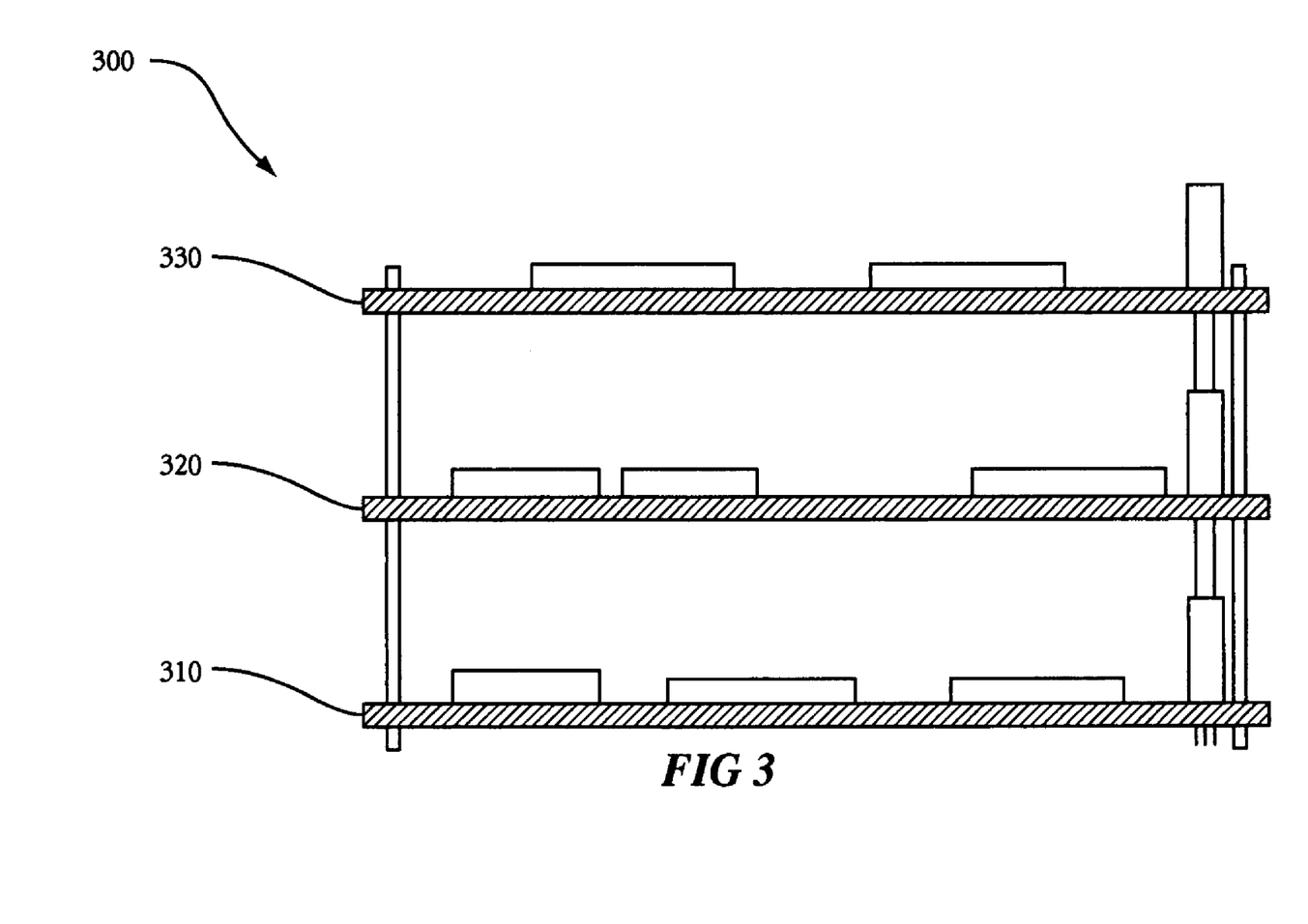
FIG. 3 is a diagrammatic front elevation view of the compact circuitry of a LAHMP.

A preferred aspect of the apparatus of the invention is shown in FIG. 3. The LAHMP, shown generally by the numeral 300, can be implemented with three stacked circuit boards of dimension 90 mm by 96 mm and 50 mm high and would weigh less than a pound. This conforms to the well-developed PC/104 industry standard for embedded computer systems with three stackable modules. The modules function as highly integrated components, plugged into custom carrier boards that contain application-specific interfaces and logic. The modules' self-stacking bus can be useful for installing multiple modules in one location. This facilitates future product upgrades or options, and allows temporary addition of modules during system debug or test. The bottom circuit board 310 is a single board PC/104 computer. The middle card 320 is a four-channel data acquisition card, including A/D conversion. The top card 330 includes required amplifiers and required band pass filters for conditioning the raw data before processing. After packaging in an electronic enclosure as would be needed in a military application the entire LAHMP module should be only about 100×100×40 mm and weighs less than 400 grams. It should be recognized that if a larger transducer array system is needed that 8 channel cards can be fitted into the PC/104 format or another data acquisition card could be added to the stack with a modest increase in height. Alternately an additional card could be added to handle wireless transmission.

Figure 4:
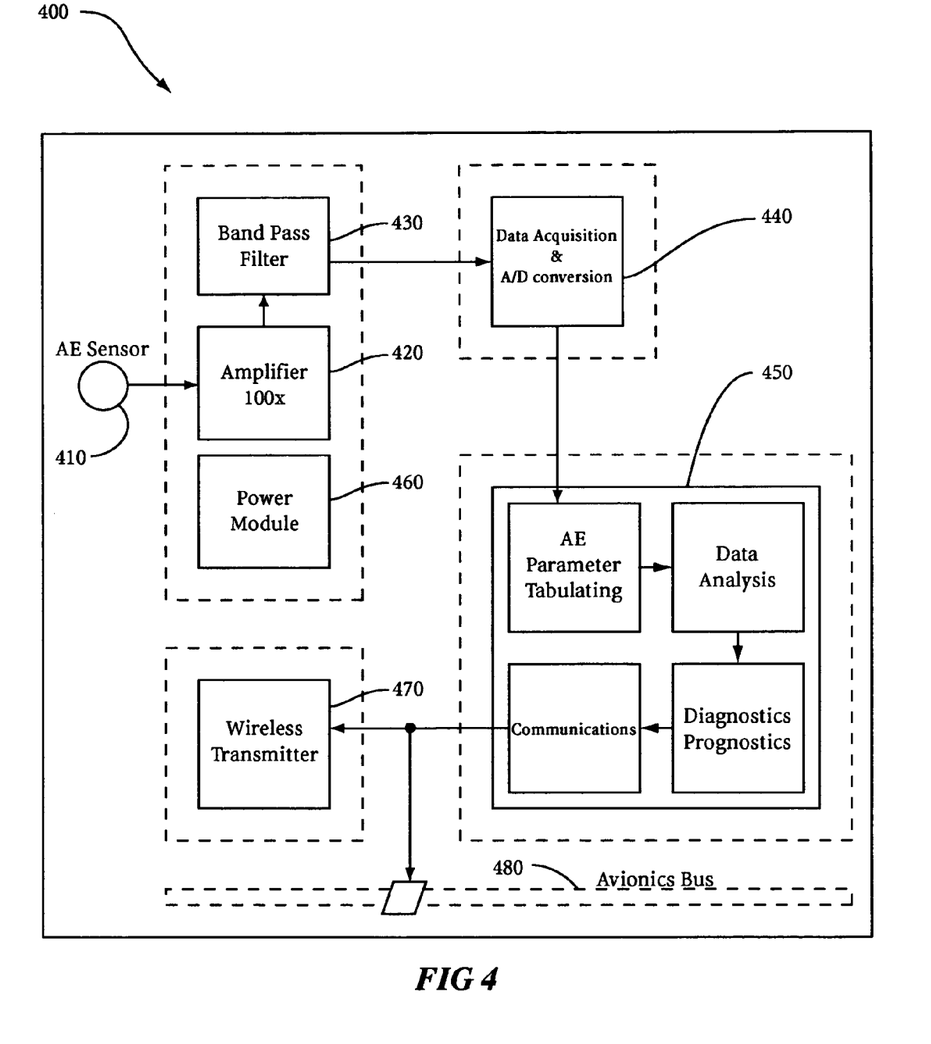
FIG. 4 is a representation of the flow of information through the LAHMP.

Another important aspect of the instant invention is the software approach which allows the normally data processing intensive acoustic emission analysis to be easily fit onto the small PC/104 format. A typical acoustic emission transducer sends about 10 million samples per second to a central computer. In the implementation of the instant invention this data is neither stored nor forwarded in the PC/104 format microcomputer but is instead discarded continuously after being processed. The method for processing the raw acoustic emission data can be described as follows. Referring to FIG. 4 the raw AE data from a single transducer is illustrated. Although only one transducer is shown for simplicity of explanation, each LAHMP system will be multi-channel as needed for the application. The raw AE data from a transducer 410 flows to the first module of the LAHMP and is first amplified in 420 and then passed through a band pass filter 430 to eliminate signals below and above a desired range. For a typical application this filter may cut off frequencies below 50 KHz and above 500 KHz. This range would be different for different materials. The raw data is then converted from analog to digital in 440 and fed into the first phase of software analysis. Also shown in FIG. 4 is a power module 460 for converting whatever local source voltage is available to a preferred 5V power to power most of the electronics. An optional wireless transmitter 470 is shown for transmitting the numerical rating of the health of the region of the structure monitored by AE transducer 410. A number of wireless technologies, such as various radio frequency transmitters, WIFI, Bluetooth, or inductive coupling are possible and anticipated by the instant invention. A microcomputer with its associated memory and software is represented by module 450. Included in microcomputer module 450 is communications hardware for communicating to the outside world. This communications hardware could be based on USB, RS-485, Ethernet, standard parallel or serial ports, VGA, LCD display, LED display, or other standards. The invention anticipates any of these. Also shown is the possibility of an electronics bus for carrying results from the microcomputer to other locations. Shown as 480 is an avionics bus as might be used on an aircraft. The electronics bus could be based on MIL STD 1553, MIL-STD-1773, ARINC-429, ARINC-575, or on any Controller Area Network (CAN)-based system such as CANOpen or DeviceNet.

Figure 5:
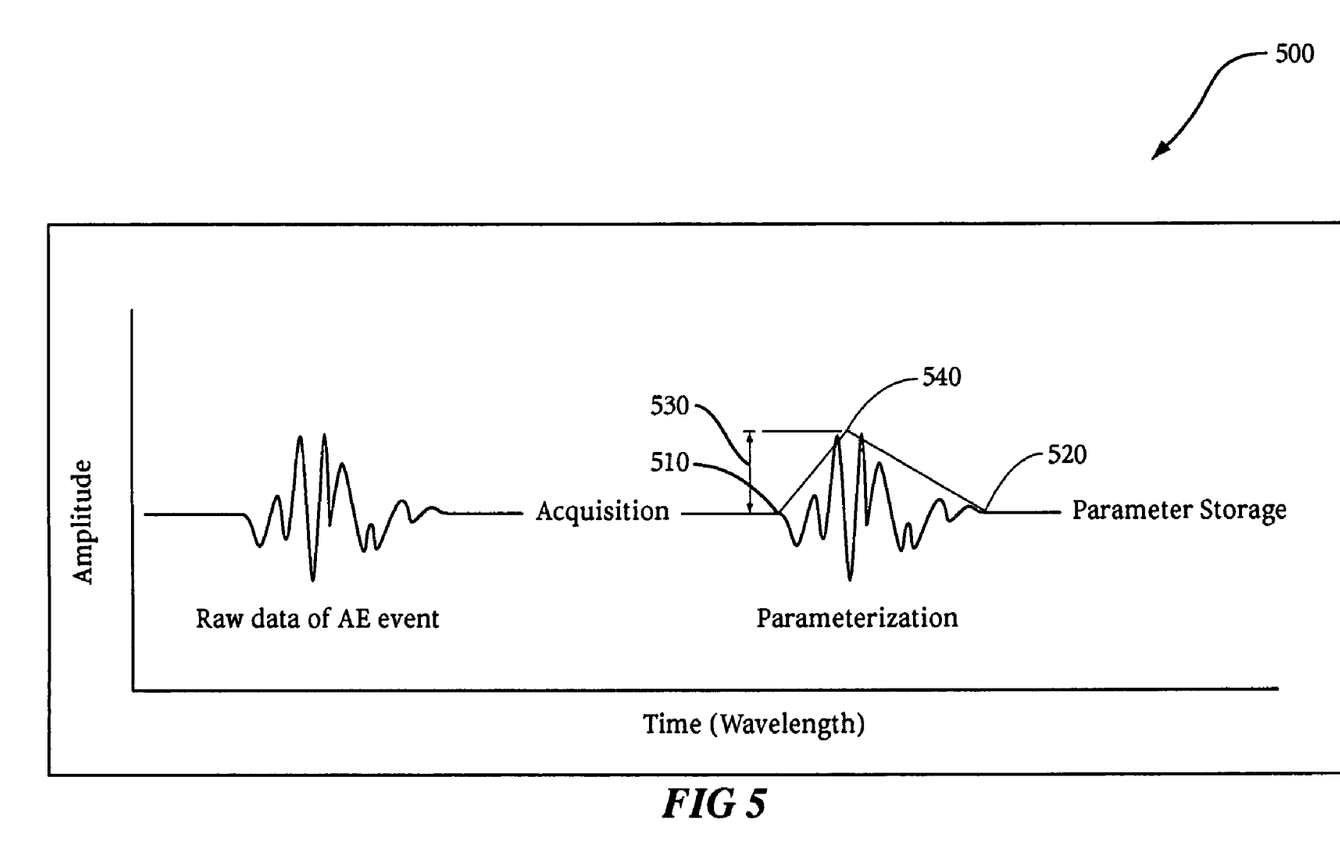
FIG. 5 is a representation of the acquisition of the amplified and filtered transducer signals and their first breakdown into AE event envelopes.

The first step of the software methodology is the acquisition of the amplified and filtered signal and the acquisition of the acoustic emission events in a simplified format as shown in FIG. 5. The software accepts amplified and filtered signals for a prescribed period, for example five minutes, and analyzes for AE events based on a prescribed threshold voltage that is application specific. When an AE event occurs, that is, when the first instance of a threshold voltage is exceeded, an event envelope, as depicted by the triangle, is calculated. The threshold voltage defines the width of the AE events by finding the start and stop times for each event.

The event envelope, shown as the triangle in FIG. 5 has four parameters, start time Ti (510), stop time Ts (520), maximum amplitude Vmax (530), and time of maximum amplitude Tmax (540). Start and stop times are used to calculate the duration D of the event. Each events is paired with a channel number and (optionally) a "box number" that signifies the specific AE transducer device the signal came from. All of the envelopes for a prescribed time period are stored simply as an ASCII delimited data file on compact flash cards on the PC/104 microcomputer. All of the raw data that was used to generate those envelopes is then discarded, eliminating the need to either store massive data files on any computer system or to transmit large bandwidths of transducer data through an extensive aircraft cabling system or across an avionics bus. The compact stored ASCII delimited data files for various time periods are simply stored in flash card memory for subsequent feeding to the next software steps representing analysis, diagnosis, and prognosis.

The remaining software steps can then analyze the incoming data by single channel, multiple channels, or cumulatively (all channels), depending on user input. Four analyses are performed on the incoming data, each of which is discussed in turn. Each analysis results in a weight or score, which is ultimately tallied to arrive at an assessment of the structure's health. The specific numbers and equations used in the following are modifiable in a straightforward manner but not by the end user (i.e. changed in an ASCII text configuration file read at program startup, which can be edited).

As a first analysis step, a simple tally of all events N for a prescribed time period for the channel(s) that exceed 75 dB. These are assigned a score based on the following simple table:

TABLE 1

| Hits > 75DB | Score |
|---|---|
| <10 | 1 |
| 10–20 | 2 |
| 21–35 | 3 |
| 36–49 | 4 |
| 50–75 | 5 |
| >75 | 6 |

In a second step of analysis a historic index (HI) is calculated. This is basically a measure of current signal strengths in comparison to historical signal strengths. A parameter K is used to define HI.

TABLE 2

| Number Of Events N | K |
|---|---|
| Less than 101 | 0 |
| 101–500 | .8*N |
| Greater than 500 | N−100 |

HI is then calculated from the ratio of two sums of the signal strengths:

$$HI = \frac{N}{N-K}\left(\frac{\sum_{i=K+1}^{N} SignalStrength_i}{\sum_{i}^{N} SignalStrength_i}\right)$$

Note that for this process the Signal Strength of each event is the Vmax measured in the data acquisition step defined above in calculating the event envelope for each event.

And a score for HI is then assigned as follows:

TABLE 3

| HI | Score |
|---|---|
| <1.2 | 1 |
| 1.2–1.74 | 2 |
| 1.75–2.24 | 3 |
| 2.25–2.99 | 4 |
| 3–5 | 5 |
| >5 | 6 |

In a third step of the analysis phase the cumulative energy CE is calculated. CE is basically a measure of the area under the defined AE event. Given the 4 main parameters of an AE signal, CE is given by the following, where Di is the duration of the i-th event, Vti is the threshold voltage, and VMi is the voltage of the maximum amplitude of the i-th event.

TABLE 4

$$CE = \frac{\sum D_i(Vti + VMi)}{4}$$

| CE | Score |
|---|---|
| 500–749 | 1 |
| 750–999 | 2 |
| >1000 | 3 |

In a fourth step of the analysis phase a severity S is calculated as defined as the average of the J largest energy hits is then given as the sum of the top J events' energy divided by J, i.e.

$$S = \frac{\sum_{i}^{J} Ei}{J}$$

wherein Ei represents the Vmax of the top J events after all N events have been sorted by Vmax and where J is a number of between 10 and 50 and for most of our applications is 20.

In a fifth step of the analysis phase a comparison is made of the historical index (HI) and severity (S) data obtained in steps three and four above to predetermined severity and HI data that was obtained by research into acoustic emission experimental data from the structure material being monitored. For example, if the application was to monitor AE event data from an F-22 fighter the experimental program would have already been done to gather acoustic emission data from simulated structures of F-22 fighters. Data from that previously developed research is stored in the memory of each of the distributed microcomputer systems as a simple look-up table.

Figure 6:
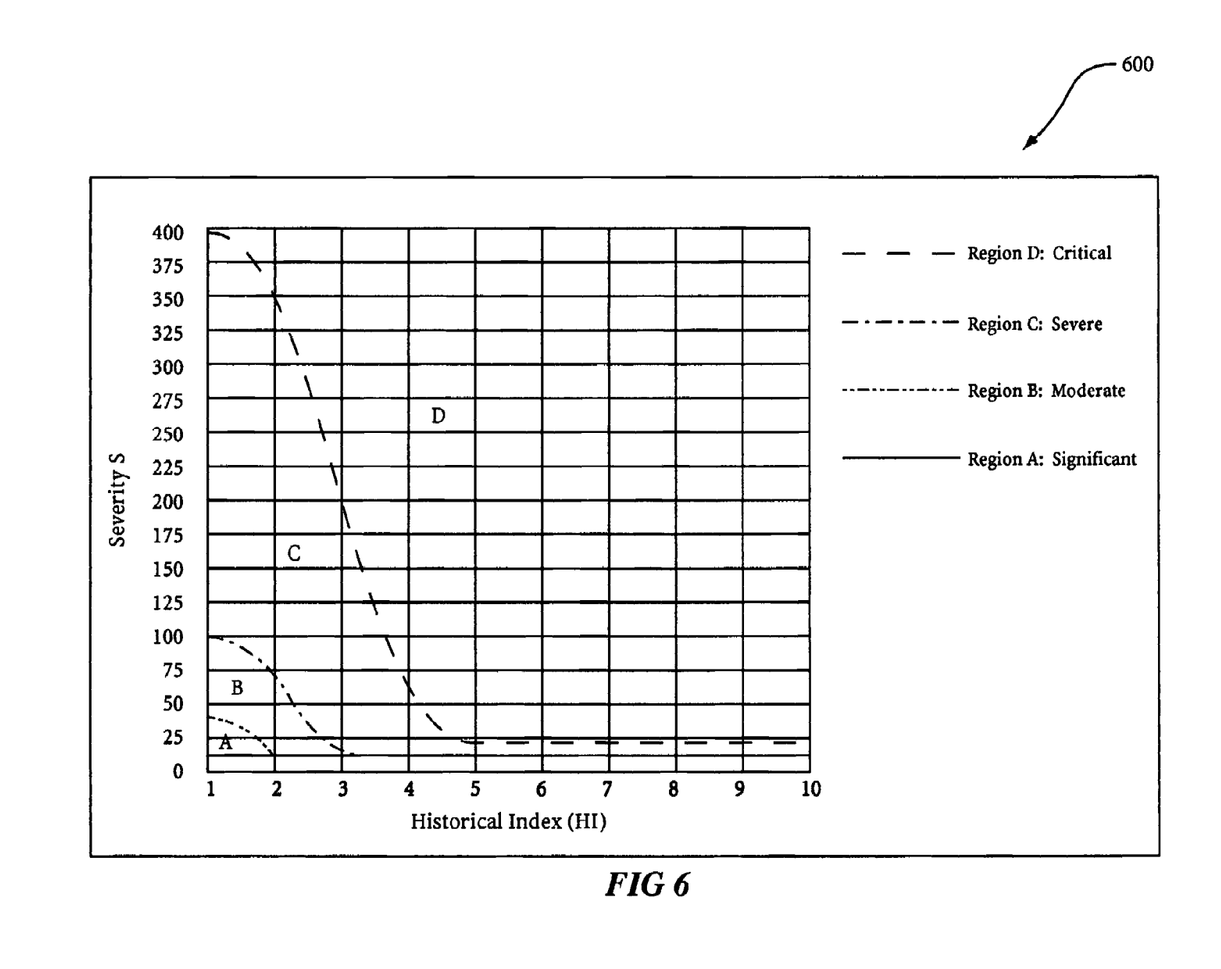
FIG. 6 is a typical severity vs historical index plot for a composite structure.

FIG. 6 is a plot showing typical results from such acoustic emission testing of aircraft structures. Severity is plotted against historical index and a series of curves developed that divide the total results up into regions ranging from "insignificant" damage to "critical" damage. By comparison of each of the most recent time intervals S and HI results to the data from the look-up table the relative damage is determined and a new fourth score is assigned from the following table.

TABLE 5

| Region | Score |
|---|---|
| "X" (Insignificant) | 1 |
| A (Significant) | 2 |
| B (Moderate) | 3 |
| C (Severe) | 4 |
| D (Critical) | 5 |

To arrive at an overall assessment of the condition of the structure then, the scores from each of the 4 criteria above are summed, to provide an overall score between 4 and 20. This score is then divided by 5 to arrive at a final assessment number with a score of 4 being the most severely damaged. Based on the previously determined research the prognosis is correlated to final recommendations as summarized in the following table.

TABLE 6

| Final Score | Assessed Condition | Comments |
|---|---|---|
| <2.4 | Insignificant | Emission source is structurally insignificant |
| 2.4–3.2 | Minor | Minor emission. Note for future reference - visually inspect accessible areas. |
| 3.2–3.7 | Significant | Significant structural defect requiring follow-up evaluation. As a minimum, evaluation should include further data analysis and visual inspection of accessible areas. Consideration should be given to comprehensive nondestructive examination, retest, and increased frequency of inspection. |
| >3.7 | Major | Major structural defect. Immediate shutdown and additional nondestructive examination. |

Thus the final assessment of the current condition of the monitored structure is characterized by a numerical rating. The software arrives at this rating without any required intervention of a human expert. This small data set (a simple digital number), can be easily stored for later retrieval, transmitted over an avionics bus or transmitted wirelessly to give a prognostic analysis with recommendations based on table 6. In the event of severe damage detection, the software can raise an alarm.

The reduction of the large amount of raw AE data, which as stated before involves multiple millions of voltage readings over a prescribed time period, is thus reduced into a final prognosis of an assessed condition of four possible ratings. This reduced data set can be easily stored on board on each distributed microcomputer for multiple missions and retrieved later, or wirelessly transmitted or moved over an electronics bus to a display at regular intervals.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

What is claimed is:

1. A method for the continued real time health monitoring of a structure using acoustic emission analysis comprising the steps of:
   a. fixedly mounting at least one acoustic emission transducer in a region of said structure to be monitored;
   b. distributing, in that same said region, a distributed health monitoring system containing all necessary hardware and software for complete analysis of the raw acoustic emission signals from said at least one transducer;
   c. amplifying the voltage signals received from said at least one acoustic emission transducer to produce an amplified signal;
   d. filtering said amplified signal to eliminate unwanted frequencies to produce a filtered signal;
   e. acquiring, during a pre-determined time period, said filtered signal to identify and record acoustic emission events;
   f. diagnosing, from said recorded acoustic emission events for said pre-determined time period, the overall health assessment of said region of said structure; wherein said diagnosing step further comprises the steps of;
      i. calculating in a first calculation, the number of acoustic emission events above a threshold decibel level;
      ii. calculating, in a second calculation, a historical index for said acoustic emission events;
      iii. calculating, in a third calculation, a cumulative energy for said acoustic emission events;
      iv. calculating, in a fourth calculation, a severity of said acoustic emission events;
      v. calculating, in a fifth calculation, a measure of relative damage by comparing said historical index and said severity to pre-determined and pre-recorded experimental acoustic emission research data; and
      vi. calculating, as a numerical rating, an overall health assessment of said region of said structure for said pre-determined time period, using the results of said first, second, third, and fifth calculations.

2. The method of claim 1 further comprising storing said numerical rating in memory of said distributed health-monitoring system for future use.

3. The method of claim 1 further comprising the step of: transmitting said numerical rating from said distributed health monitoring system to a new location.

4. The method of claim 2 wherein said transmitting step utilizes wireless transmission.

5. The method of claim 3 wherein said wireless transmission utilizes a radio frequency transmitter.

6. The method of claim 2 wherein said transmitting step utilizes an electronic bus.

7. The method of claim 5 wherein said electronics bus is an avionics bus.

8. A distributed real time health monitoring system for monitoring of acoustic emission signal from a structure using the method of claim 1 comprising:
   a. at least one acoustic emission transducer for detecting said acoustic emission signals and outputting transducer signals, said at least one acoustic emission transducer fixedly mounted to a region of said structure to be monitored; and
   b. a microcomputer system comprising:
      i. computer memory;
      ii. data acquisition software to acquire said transducer signals and record acoustic emission events; and
      iii. data analysis software to assess and classify the health of said region of said structure.

9. The distributed real time health monitoring system for monitoring of acoustic emission signals of claim 8 wherein said at least one acoustic emission transducer for detecting said acoustic emission signals is a piezoelectric ceramic acoustic emission transducer.

10. The distributed real time health monitoring system for monitoring of acoustic emission signals of claim 8 wherein said at least one acoustic emission transducer for detecting said acoustic emission signals is a piezoelectric polyvinylidene fluoride acoustic emission transducer.

11. The distributed real time health monitoring system for monitoring of acoustic emission signals of claim 8 further comprising, an amplifier system for amplifying said transducer signals to generate amplified signals.

12. The distributed real time health monitoring system for monitoring of acoustic emission signals of claim 11 further comprising a band limit filter to filter said amplified signals and generate filtered signals.

13. The distributed real time health monitoring system for monitoring of acoustic emission signals of claim 12 wherein said band limit filter limits frequencies to filtered signals between 75 and 500 kHz.

14. The distributed real time health monitoring system for monitoring of acoustic emission signals of claim 11 further comprising an analog to digital converter to convert said filtered signals to digital filtered signals.

15. The distributed real time health monitoring system for monitoring of acoustic emission signals of claim 8 wherein said microcomputer system further comprises communication circuitry to communicate externally.

16. The distributed real time health monitoring system for monitoring of acoustic emission signals of claim 15 wherein said communication circuitry is based on a RS-232 standard.

17. The distributed real time health monitoring system for monitoring of acoustic emission signals of claim 15 wherein said communication circuitry is based on a USB standard.

18. The distributed real time health monitoring system for monitoring of acoustic emission signals of claim 8 wherein said data analysis software classifies said health of said region of said structure into a numerical rating.

19. The distributed real time health monitoring system for monitoring of acoustic emission signals of claim 18 wherein said numerical rating is stored in said memory for future reference.

20. The distributed real time health monitoring system for monitoring of acoustic emission signals of claim 18 wherein said numerical rating is transmitted wirelessly to a different location.

21. The distributed real time health monitoring system for monitoring of acoustic emission signals of claim 20 wherein said numerical rating is transmitted wirelessly by a radio frequency transmitter.

22. The distributed real time health monitoring system for monitoring of acoustic emission signals of claim 18 wherein said numerical rating is transmitted via an electronic bus system.

23. The distributed real time health monitoring system for monitoring of acoustic emission signals of claim 22 wherein said electronic bus is an avionics bus on an aircraft.

24. The distributed real time health monitoring system for monitoring of acoustic emission signals of claim 23 wherein said avionics bus is based on an ARINC-429 standard.

25. The distributed real time health monitoring system for monitoring of acoustic emission signals of claim 23 wherein said avionics bus is based on a MIL STD 1553.

* * * * *